US00PP10624P

United States Patent [19]

Akerboom

[11] Patent Number: Plant 10,624

[45] Date of Patent: Sep. 29, 1998

[54] ASTER PLANT NAMED 'KARMIJN'

[75] Inventor: Petrus J. Akerboom, Ter Aar, Netherlands

[73] Assignee: De Nachtvlinder B.V., Ter Aar, Netherlands

[21] Appl. No.: 664,520

[22] Filed: Jun. 17, 1996

[51] Int. Cl.[6] ..... A01H 5/00

[52] U.S. Cl. ..... Plt./68.1

[58] Field of Search ..... Plt./68.1

[56] References Cited

PUBLICATIONS

UPOV Rom Disk 1996/03 Search Results 3 pages, 1996.

*Primary Examiner*—Howard J. Locker
*Assistant Examiner*—Kent L. Bell
*Attorney, Agent, or Firm*—Foley & Lardner

[57] ABSTRACT

A new and distinct cultivar of aster plant designated 'Karmijn' is short in height as flowering commences; produces dark green leaves without anthocyanin that are obovate in shape, and a flower head that is small to medium in size with many purple-violet ray florets that are narrowly elliptic in shape.

2 Drawing Sheets

The present invention comprises a new and distinct cultivar of aster plant hereinafter referred to by the cultivar name 'Karmijn'.

The new cultivar was originated from a cross made by the inventor in a controlled breeding program in Ter Aar, The Netherlands. The female or seed parent was a selection from proprietary breeding stock designated the "Butterfly family" while the male or pollen parent was a selection from proprietary breeding stock designated the "P" family.

'Karmijn' was discovered and selected by the inventor as a flowering plant within the progeny of the stated cross in a controlled environment in Ter Aar, The Netherlands. Asexual reproduction of the new cultivar by cuttings, as performed by the inventor at Ter Aar, The Netherlands for the first time in April 1993, and continuing thereafter, has demonstrated that the combination of characteristics as herein disclosed for the new cultivar are firmly fixed and retained through successive generations of asexual reproduction.

'Karmijn' has not been observed under all possible environmental conditions. The phenotype may vary with variations in environment such as temperature, light intensity and day-length, without a change in the genotype of the plant. The following observations, measurements and values describe the new cultivar as grown in Bet Dagan, Israel, under conditions which closely approximate those generally used in commercial practice.

The following traits have been repeatedly observed and are determined to be basic characteristics of 'Karmijn', which in combination distinguish this aster as a new and distinct cultivar:

1. The plant height is short as flowering commences.
2. The leaves are obovate shaped, of medium length and dark green in color without anthocyanin coloration.
3. The first flower heads produced are spread along the axis.
4. The flower head is small to medium in size with many ray florets.
5. The ray florets are medium in length and narrowly elliptic in shape.
6. The involucre is campanulate in shape and medium in length.
7. The flower response is medium compared to other aster cultivars.

The new cultivar is most similar to 'Milka' (U.S. plant patent application Ser. No. 08/664,519) and 'Parade' (U.S. plant patent application Ser. No. 08/664,669), both of which are described in co-pending applications of the inventor. Each of these cultivars produces flowers with many ray florets and a similar type of flower head. The cultivars differ, however, with respect to flower color, speed of growth, plant height, leaf shape and leaf length.

The following Table provides several phenotypic characteristics that can be used to distinguish the aster varieties 'Parade', 'Milka' and 'Karmijn'.

| | Ray Florets | | | Capitulum | |
|---|---|---|---|---|---|
| | Colors (RHS) | Length (mm) | Diameter (mm) | Diameter (mm) | Involucre Shape |
| 'Parade' | Purple (87A) | 11–13 | 1.8 | 28–30 | Funnel-shaped, Long |
| 'Milka' | Violet (85A) | 14–16 | 2.0 | 24–27 | Cylindrical, Very Long |
| 'Karmijn' | Purple-Violet (81B) | 12–15 | 2.0 | 26–29 | Campanulate, Medium Length |

The accompanying photographs show a typical specimen plant of the new cultivar. The colors appearing in the photographs are as true as possible with color illustrations of this type.

Sheet 1 is a side view of 'Karmijn' while

Sheet 2 is a close-up of a flower from the new variety.

In the following description, color references are made to The Royal Horticultural Society Color Chart (R.H.S.), except where general colors of ordinary significance are referred to. Color values were taken indoors in a north light in Bet Dagan, Israel.

Botanical classification:

*Species name.*—Aster Novi-Belgii L.

*Cultivar name.*—'Karmijn'.

Parentage:

*Male parent.*—Proprietary selection from the P family.

*Female parent.*—Proprietary selection from the Butterfly family.

Propagation: The new cultivar holds its distinguishing characteristics through successive asexual reproduction by cuttings.

Inflorescence:

A. Capitulum:

*Form.*—Convex.

*Type.*—Double.
*Diameter across face.*—26–29 mm.

B. Corolla of ray florets:
*Color* (*general tonality from a distance of three meters*).—Purple.
*Color* (*upper surface*).—Purple-violet (R.H.S. 81B).
*Color* (*under surface*).—Same as upper surface.
*Shape.*—Narrow elliptic, rounded apex.
*Size.*—12–15 mm in length and 2.0 mm in width.
*Number of ray florets.*—136–162 per flower.

C. Corolla of disc florets: 'Karmijn' does not produce disc florets.

D. Reproductive organs:
*Androecium.*—Absent.
*Gynoecium.*—Present.

E. Buds:
*Size.*—7–8 mm diameter just before opening.
*Color.*—Color of flower petals as the bud opens is 81B.
*Arrangement.*—At acute angle relative to supporting stem.

Plant

A. General appearance: 'Karmijn' grows to a medium height depending on the light intensity, but can reach a height of 2 meters under continuous (up to 13½ hours) long-day conditions. The branches of 'Karmijn' are average in number density, and hairs on the stem are absent or very weak.

B. Foliage:
*Color.*—Dark green, R.H.S. 137A-B.
*Shape.*—Obovate.
*Margin.*—Dentations on distal part of margin.
*Size.*—With regard to the following description, the first internode is found at the location of the first side flower under the top flower. Length: 5th internode: 31–38 mm. 10th internode: 38–60 mm. 15th internode: 69–75 mm. 20th internode: 77–104 mm. Width: 5th internode: 4.2–6.1 mm. 10th internode: 7.3–8.6 mm. 15th internode: 11.0–12.6 mm. 20th internode: 13.8–15.4 mm.

C. Stem:
*Length.*—5th internode: 12–15 mm. 10th internode: 19–23 mm. 15th internode: 21–24 mm. 20th internode: 24–31 mm.
*Thickness.*—5th internode: 1.5–1.9 mm. 10th internode: 2.3–3.0 mm. 15th internode: 2.9–3.5 mm. 20th internode: 3.5–4.0 mm.

D. Side branch:
*Length.*—5th internode: 54–70 mm. 10th internode: 81–102 mm. 15th internode: 118–135 mm. 20th internode: 176–212 mm.

E. Disease resistance: No abnormal disease problems have been noted to date. Accordingly, the disease resistance exhibited by this cultivar when compared to other known commercial aster varieties is not unique. However, the cultivar does appear to exhibit some resistance to tomato spotted wilt virus.

F. Fertility: Does not produce pollen.

I claim:

1. A new distinct cultivar of aster plant named 'Karmijn', as illustrated and described herein.

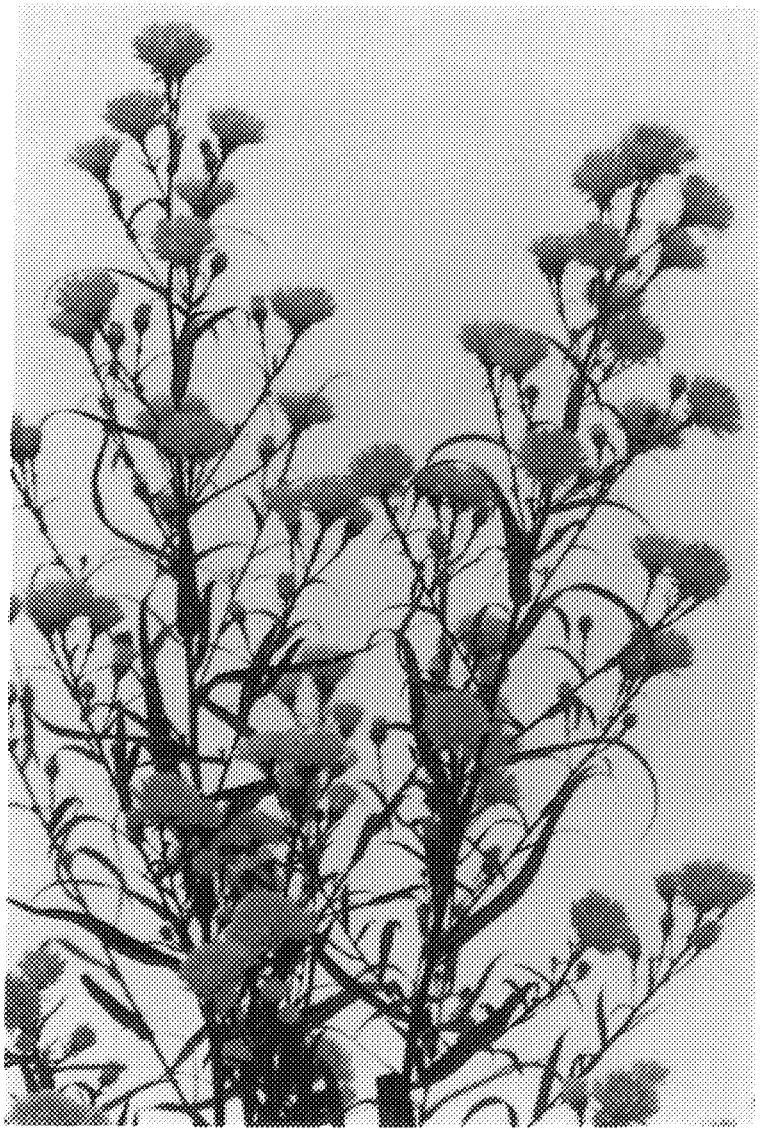

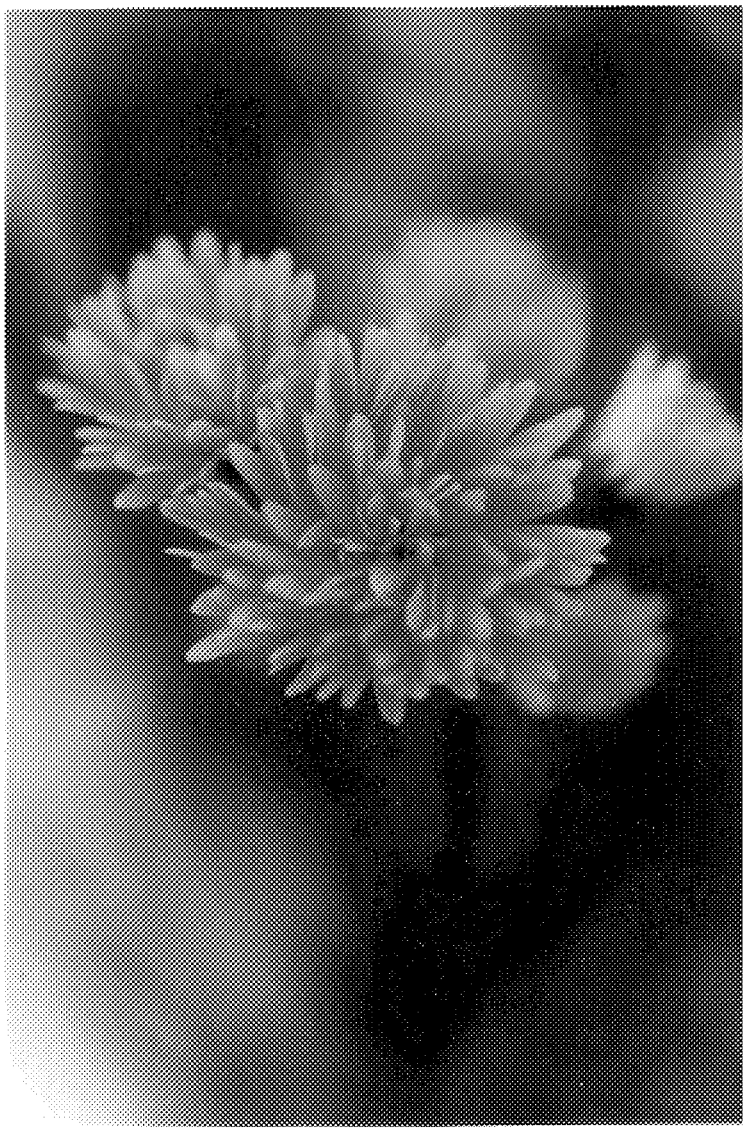

* * * * *